(12) United States Patent
Xu

(10) Patent No.: US 9,604,991 B2
(45) Date of Patent: Mar. 28, 2017

(54) PREPARATION METHOD OF TICAGRELOR AND INTERMEDIATES THEREOF

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 14/975,785

(22) Filed: Dec. 20, 2015

(65) Prior Publication Data

US 2016/0102101 A1    Apr. 14, 2016

Related U.S. Application Data

(63) Continuation of application No. PCT/CN2014/079228, filed on Jun. 5, 2014.

(30) Foreign Application Priority Data

Jun. 24, 2013 (CN) .......................... 2013 1 0251364
Jun. 26, 2013 (CN) .......................... 2013 1 0258158
Jun. 27, 2013 (CN) .......................... 2013 1 0260749

(51) Int. Cl.
   *C07D 471/00*   (2006.01)
   *C07D 487/00*   (2006.01)
   *C07D 491/00*   (2006.01)
   *C07D 487/04*   (2006.01)
   *C07D 317/44*   (2006.01)
   *C07D 405/04*   (2006.01)

(52) U.S. Cl.
   CPC ......... *C07D 487/04* (2013.01); *C07D 317/44* (2013.01); *C07D 405/04* (2013.01)

(58) Field of Classification Search
   None
   See application file for complete search history.

(56) References Cited

U.S. PATENT DOCUMENTS

| 2010/0069408 A1 | 3/2010 | Hardern et al. |
| 2011/0071290 A1 | 3/2011 | Quittman et al. |

FOREIGN PATENT DOCUMENTS

| CN | 1159442 A | 9/1997 |
| CN | 1334816 A | 2/2002 |
| CN | 1431992 A | 7/2003 |
| CN | 101495442 A | 7/2009 |
| CN | 101495444 A | 7/2009 |
| CN | 102249929 A | 11/2011 |
| CN | 102250097 A | 11/2011 |
| CN | 102311437 A | 1/2012 |
| CN | 102659825 A | 9/2012 |
| CN | 102675321 A | 9/2012 |
| CN | 102796007 A | 11/2012 |
| CN | 102924457 A | 2/2013 |
| CN | 103130726 A | 6/2013 |
| CN | 103288836 A | 9/2013 |
| CN | 103304535 A | 9/2013 |
| CN | 103304545 A | 9/2013 |
| EP | 2570405 A1 | 3/2013 |
| WO | 9703084 A1 | 1/1997 |
| WO | 9905142 A1 | 2/1999 |
| WO | 9905143 A1 | 2/1999 |
| WO | 0034283 A1 | 6/2000 |
| WO | 0136421 A1 | 5/2001 |
| WO | 0136438 A1 | 5/2001 |
| WO | 0192263 A1 | 12/2001 |
| WO | 2005095358 A2 | 10/2005 |
| WO | 2007093368 A1 | 8/2007 |
| WO | 2010003224 A1 | 1/2010 |
| WO | 2010030224 A1 | 3/2010 |
| WO | 2011017108 A2 | 2/2011 |
| WO | 2011101740 A1 | 8/2011 |
| WO | 2011132083 A2 | 10/2011 |
| WO | 2012001531 A2 | 1/2012 |
| WO | 2012085665 A2 | 6/2012 |
| WO | 2012138981 A2 | 10/2012 |
| WO | 2012139455 A1 | 10/2012 |
| WO | 2012172426 A1 | 12/2012 |
| WO | 2013037942 A1 | 3/2013 |

OTHER PUBLICATIONS

Broggi, J. et al, "Click Azide-Alkyne Cycloaddition for the Synthesis of D(−)-1, 4-Disubstituted Triazolo-Carbanucleosides" European Journal of Organic Chemistry, vol. 26, Feb. 26, 2009 (Feb. 26, 2009), 1880-1888.

*Primary Examiner* — Jeffrey H Murray
(74) *Attorney, Agent, or Firm* — Perkins Coie LLP

(57) ABSTRACT

Disclosed in the present invention is a method for preparing Ticagrelor (I), comprising the following steps: a cyclization reaction of 5-amino-1,4-di-substituted-1,2,3-triazole (II) and dialkyl carbonate (III), to obtain 9-substituted-2,6-dihydroxy-8-azapurine (IV); chlorination of intermediate (IV), to obtain 9-substituted-2,6-dichloro-8-azapurine (V); an amination reaction of intermediate (V) and trans-(1R,2S)-2-(3, 4-difluorophenyl)cyclopropanamine (VI) generates 9-substituted-6-amino-substituted-2-chloro-8-azapurine (VII); and a propanethiolation reaction of intermediate (VII) and propanethiol (VIII), to obtain Ticagrelor (I). The preparation method is simple in process, has a high chemical and chiral purity and provides a new preparation method for industrializing Ticagrelor. In addition, also provided in the present invention are intermediates of Ticagrelor and a preparation method thereof, wherein raw materials of the preparation method are easily available, the conditions thereof are mild, and the yield thereof is high.

11 Claims, No Drawings

PREPARATION METHOD OF TICAGRELOR AND INTERMEDIATES THEREOF

CROSS REFERENCE TO RELATED APPLICATIONS

This application is a continuation of and claims priority to PCT/CN2014/079228 filed 2014 Jun. 5, which claims priority to CN 201310251364.2 filed 2013 Jun. 24, CN 201310258158.4 filed 2013 Jun. 26 and CN 201310260749.5 filed 2013 Jun. 27, all of which are incorporated herein by reference.

TECHNICAL FIELD

This invention relates to the technical field of organic synthesis route design and preparation of API and intermediates, in particular, to the method for preparing Ticagrelor and intermediates thereof.

BACKGROUND ART

Ticagrelor is a novel, selective micromolecule anti-clotting drug developed by AstraZeneca. It is also the first reversibly-binding oral P2Y12 adenosine diphosphate receptor antagonist, having significantly inhibitory effect for ADP-induced platelet aggregation. It can effectively improve the symptoms of patients with acute coronary artery disease. This drug was approved by EMEA and US FDA to sell on the markets in EU countries and the United States in 2010 and 2011 respectively. Its imported preparation Ticagrelor tablets have been approved in the markets in china by China Food and Drug Administration (CFDA).

Ticagrelor chemical name: (1S,2S,3R,5S)-3-[7-[(1R,2S)-2-(3,4-difluorophenyl)cyclopropylamino]-5-(prop-mercapto-)-3H-[1,2,3]triazolo[4,5-d]pyrimidin-3-yl]-5-(2-hydroxyethoxy)cyclopentane-1,2-diol.

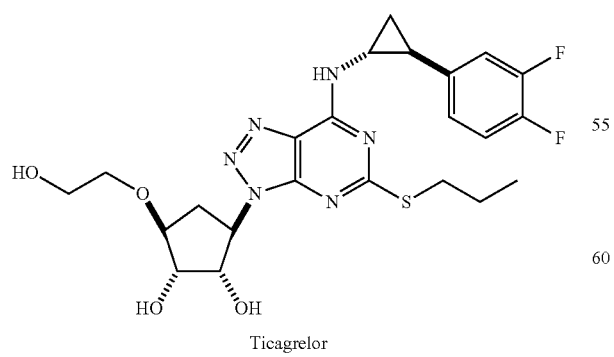

Ticagrelor

The synthesis route and preparation method of Ticagrelor have been reported. By investigating the disclosed synthesis route and preparation method, it is found that although the routes are different, most processes adopt the different chemical reactions, different reaction orders, and different linking modes of following three intermediates A, B and C to prepare Ticagrelor.

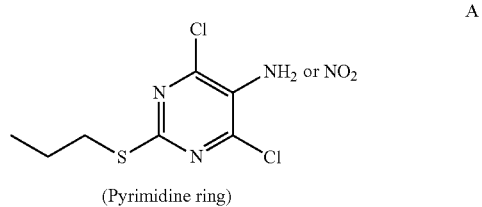

(Pyrimidine ring)

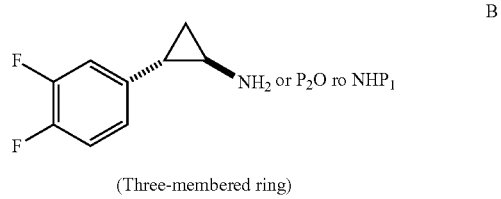

(Three-membered ring)

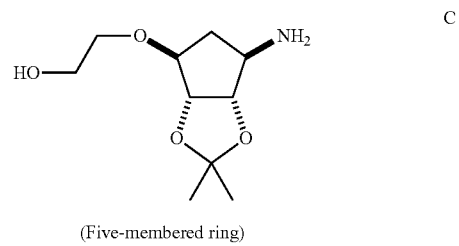

(Five-membered ring)

The synthesis route of patents WO9703084, WO99/05142, WO2000/34283 and WO2012/138981 is described as follows:

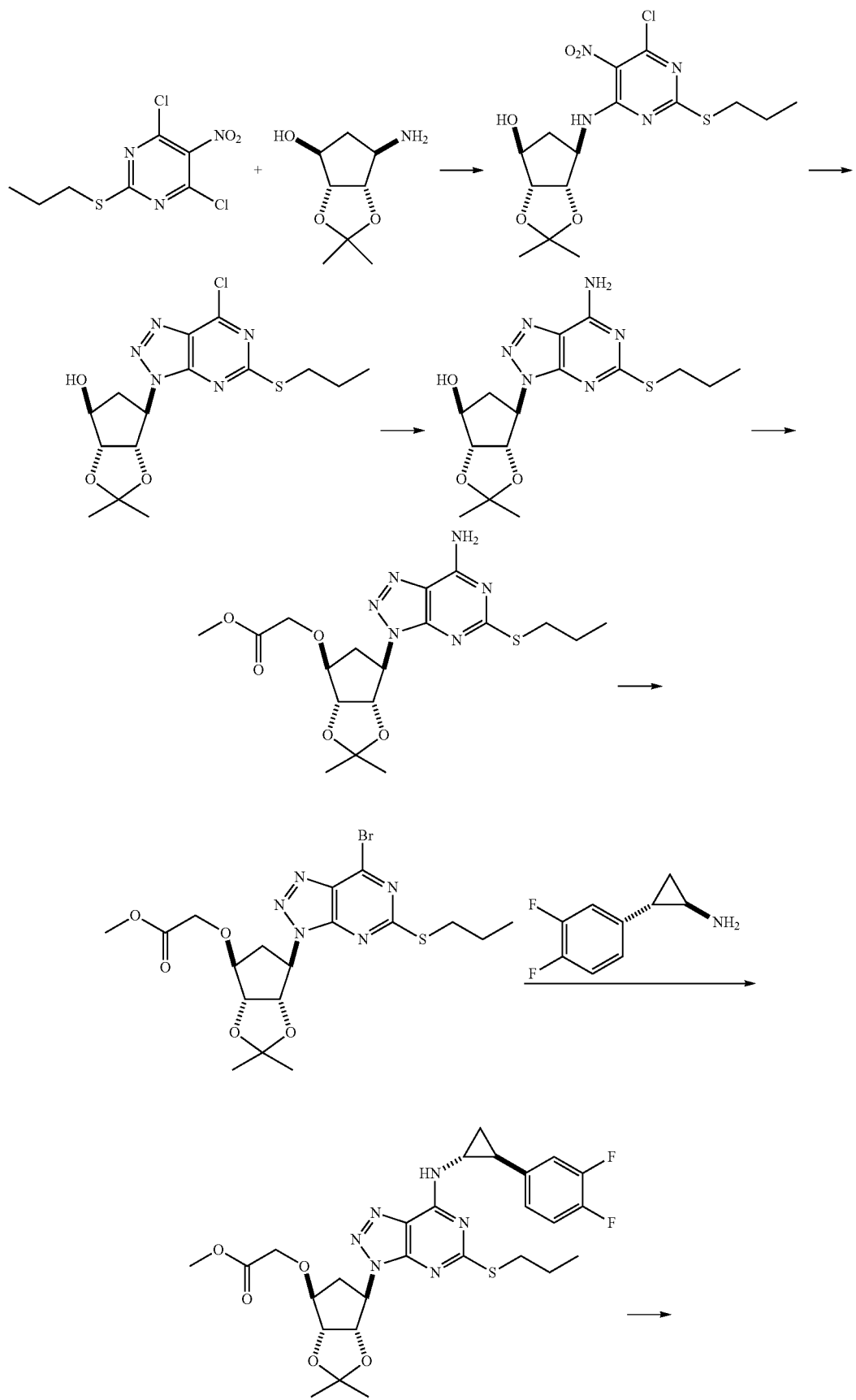

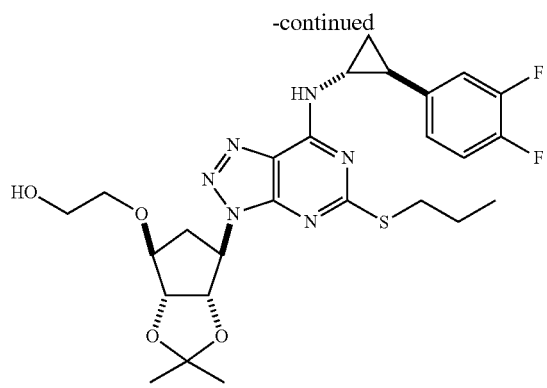

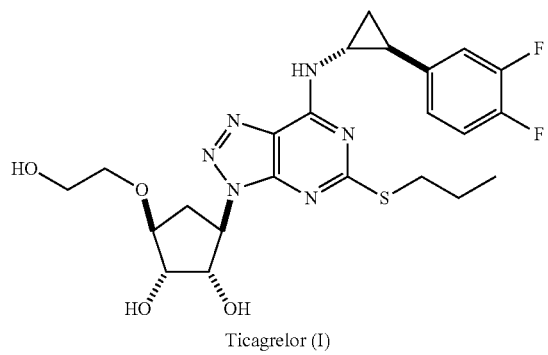

Ticagrelor (I)

The difference between the synthesis method in patent WO2001/36421, WO2001/36438 WO2011/017108 and above route is first introduction of 2-alcohol functional group in five-membered ring and reduction of nitro in pyrimidine ring to amino. In addition, in the patent WO2012/139455 and CN102675321, considering the possible side reaction in subsequent reactions of 2-alcohol functional group, hydroxyl group is firstly protected, and then amine substitution reaction is performed, and finally to generate Ticagrelor by deprotection.

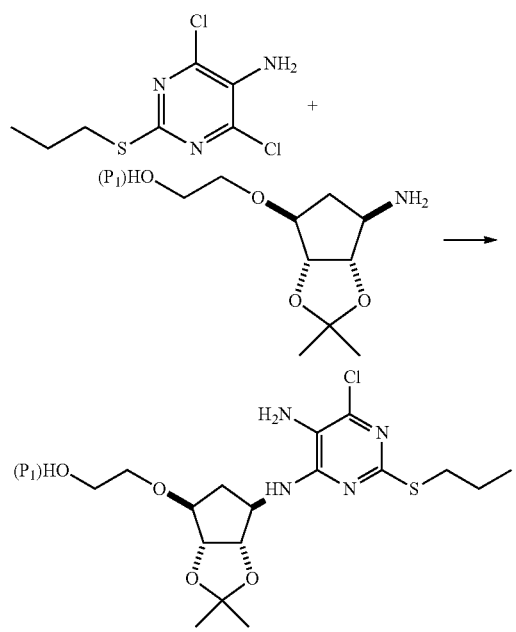

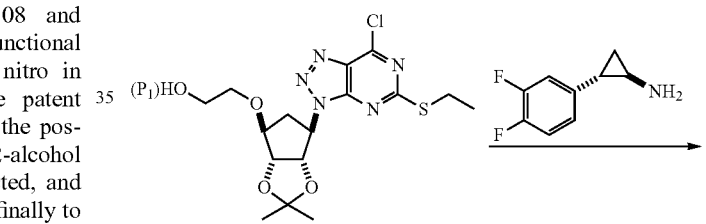

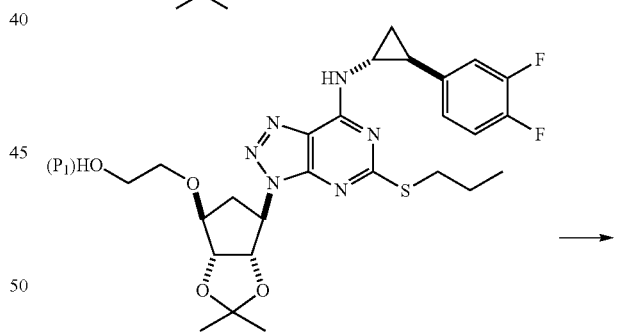

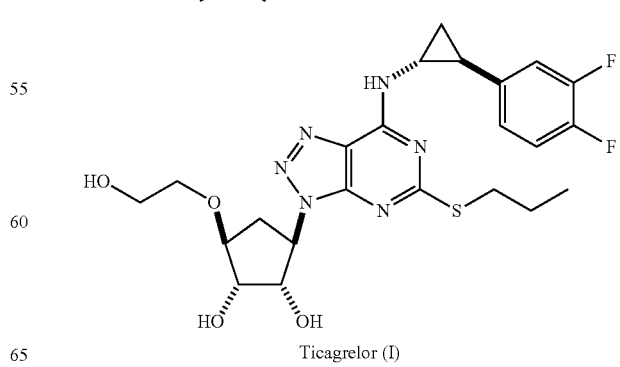

Ticagrelor (I)

In the Patent WO2012/172426, methyl acetate functional group is retained in the five-membered ring, and after completing linking of three intermediates, the ester group is reduced to alcohol.

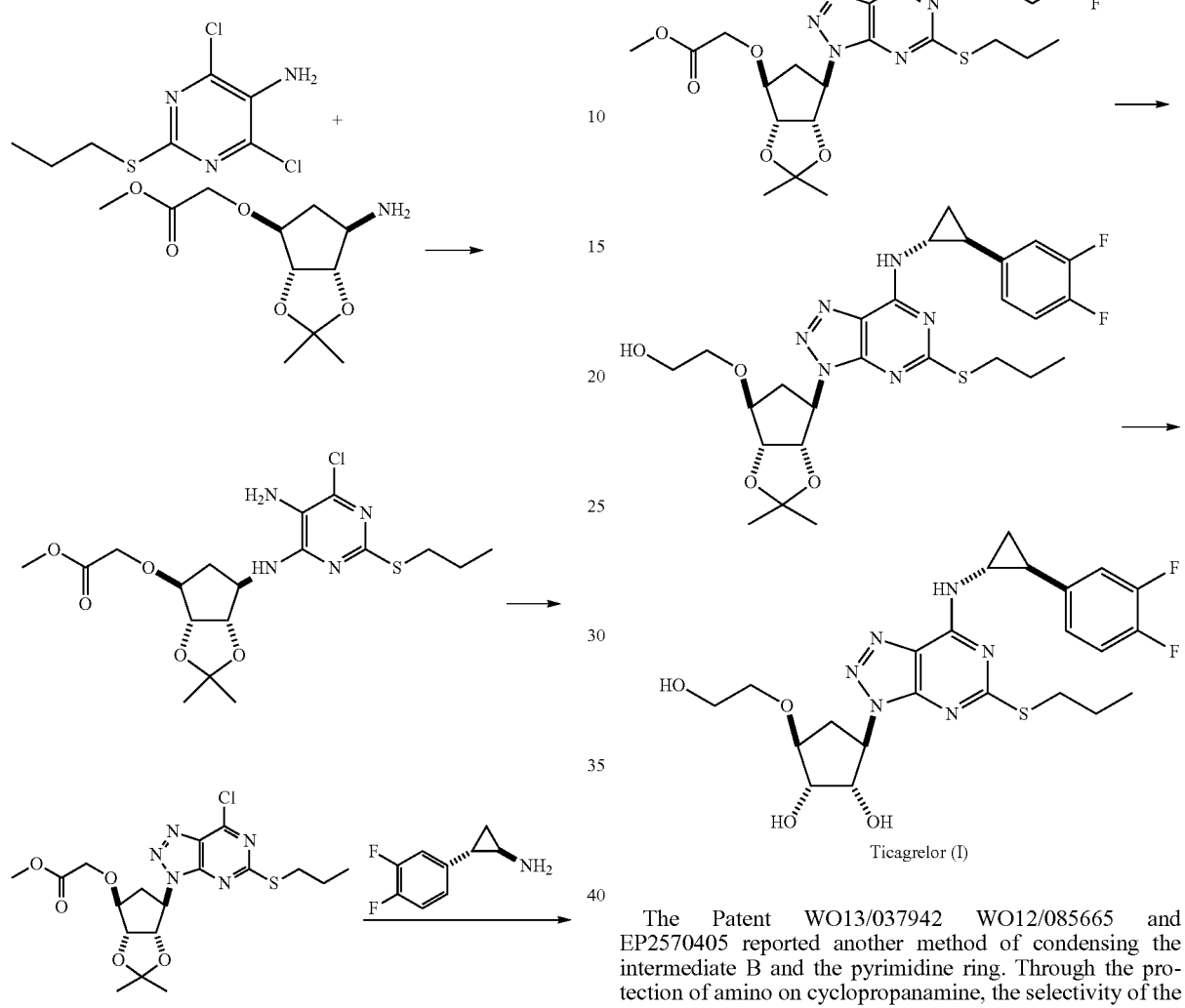

Ticagrelor (I)

The Patent WO13/037942 WO12/085665 and EP2570405 reported another method of condensing the intermediate B and the pyrimidine ring. Through the protection of amino on cyclopropanamine, the selectivity of the condensation reaction increases.

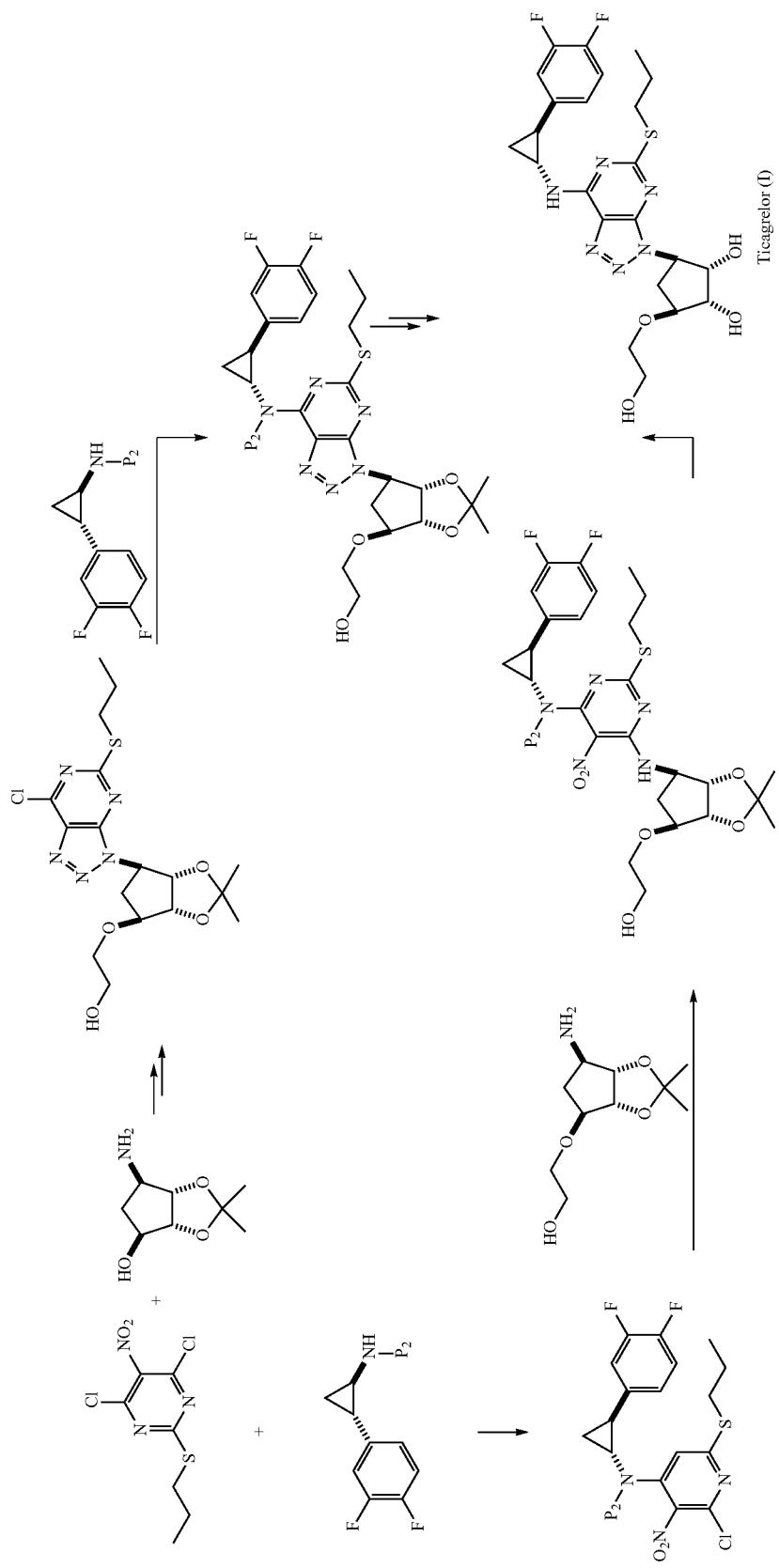

Patent CN102311437 proposed another idea for the method of linking five-membered ring (Intermediate C) with the pyrimidine ring and triazole (Intermediate A). It achieves coupling through the hydroxyl group on the five-membered ring and nitrogen atoms on triazole with the actions of triphenylphosphine and diethyl azodicarboxylate. However, due to the direction of triazole ring, the coupling position is difficult to control.

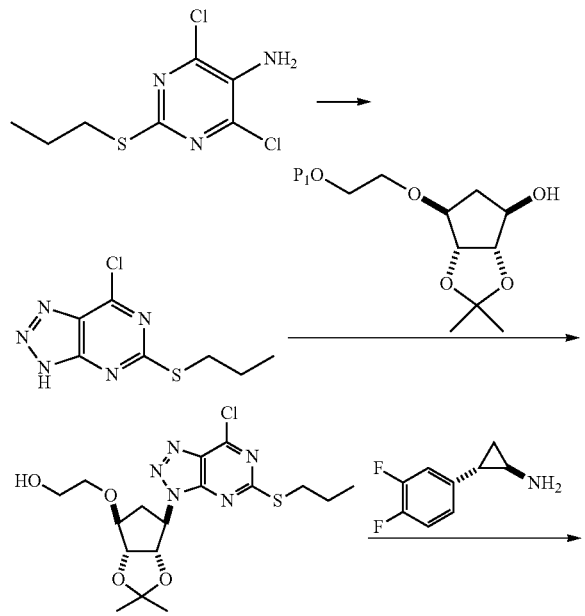

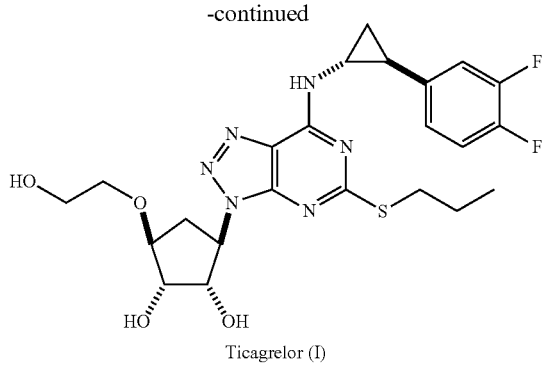

Ticagrelor (I)

In addition, patents CN103130726, CN102250097, WO2011/101740, US2011/071290, WO2010/03224, WO2007093368 and WO2005/095358 studied the method for preparing Ticagrelor pyrimidine ring (Intermediate A). Patents WO2012/001531, WO2011/132083, CN1431992, CN1334816, CN101495444, CN101495442, CN102796007 and CN102249929 studied the method for preparing Ticagrelor three-membered ring (Intermediate B); and patents WO2010/030224, US2010/069408 and CN102659815 focused on the synthesis and preparation method of Ticagrelor five-membered ring (Intermediate C).

In summary, up to now, all published literatures on the preparation of Ticagrelor focused on the preparation, protection, linking and reactions of three important intermediates (intermediates A, B and C). To seek new intermediates and synthetic routes to facilitate the preparation of Ticagrelor in a simple, economic and environmental way is essential to the economic and technological development of the API.

SUMMARY OF THE INVENTION

The main objective of the present invention is to overcome the disadvantages of the prior art, and provide an improved method for preparing Ticagrelor according to the concept of green chemistry synthesis. The preparation method is simple, economical and environmentally friendly, which can facilitate the industrial production of the drugs and promote the economical and technological development of the API.

In order to achieve the above objectives, the present invention is embodied by the follow technical solution: A method for preparing Ticagrelor (I), (I)

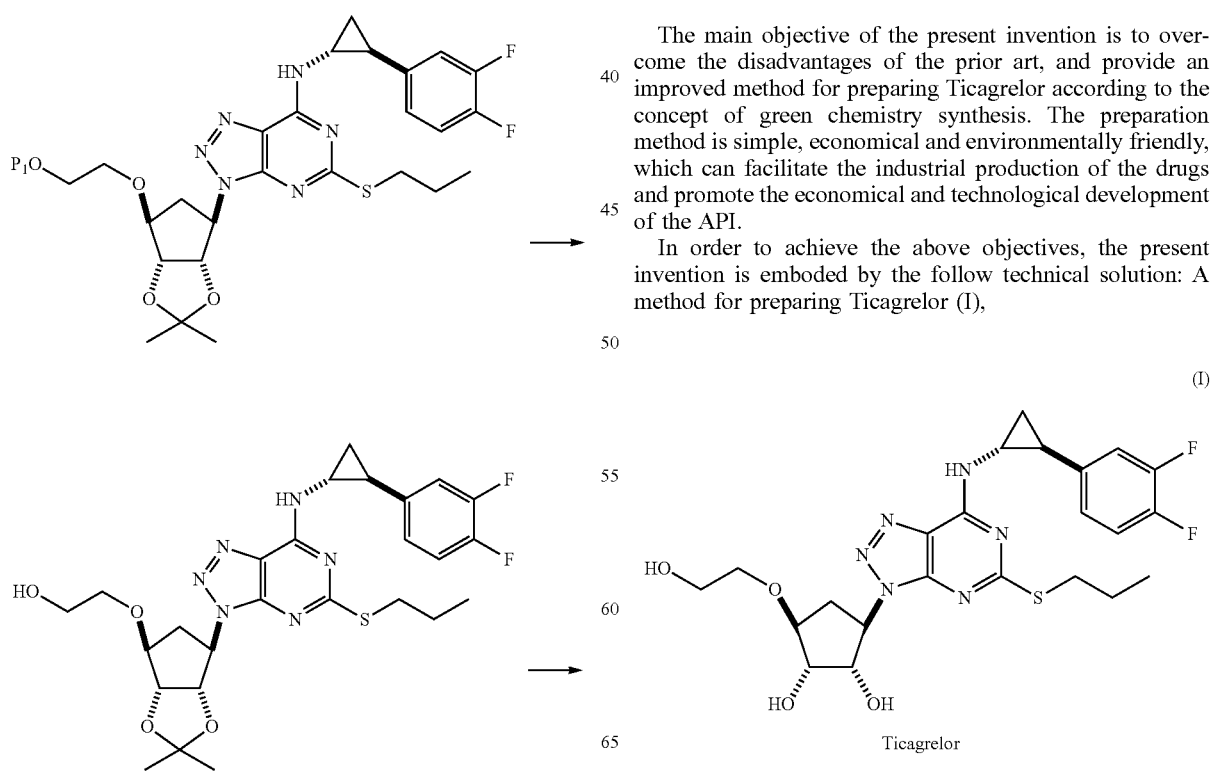

Ticagrelor wherein the preparation method comprises the following steps: a cyclization reaction of 5-amino-1,4-di-substituted-1,2,3-triazole (II) and dialkyl carbonate (III), to obtain 9-substituted-2,6-dihydroxy-8-azapurine (IV); chlorination of intermediate (IV), to obtain 9-substituted-2,6-dichloro-8-azapurine (V); an amination reaction of intermediate (V) and trans-(1R,2S)-2-(3,4-difluorophenyl)cyclopropanamine (VI) generates 9-substituted-6-amino-substituted-2-chloro-8-azapurine (VII); and a propanethiolation reaction of intermediate (VII) and propanethiol (VIII), to obtain Ticagrelor (I).

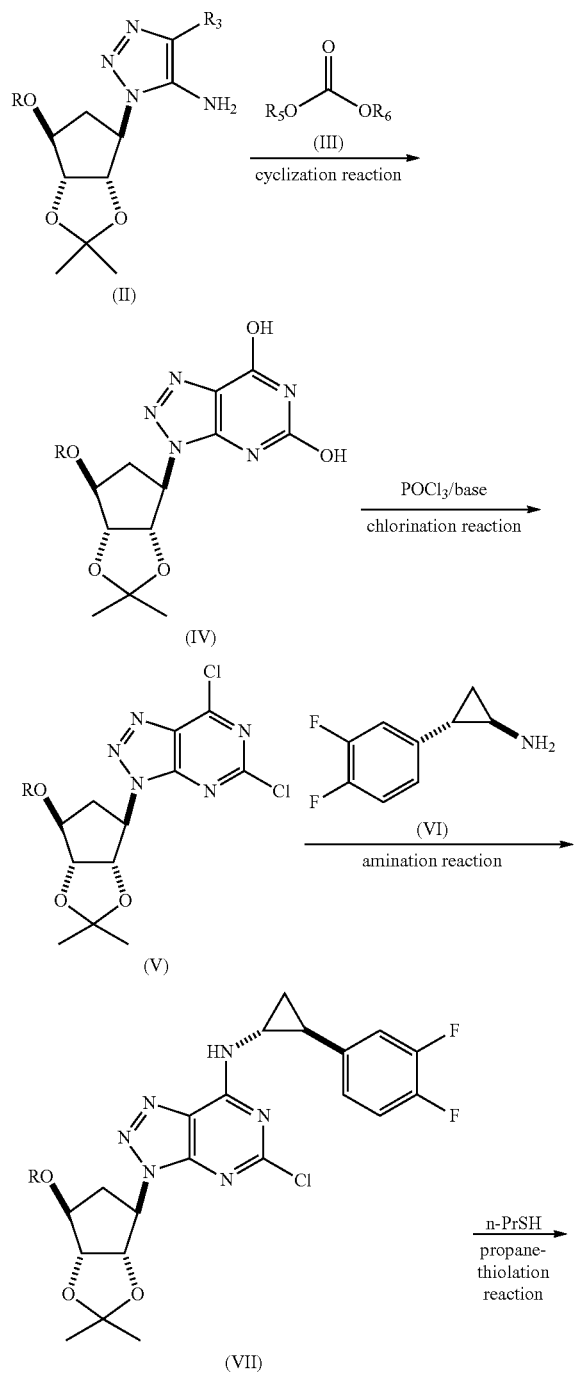

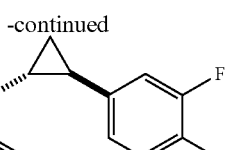

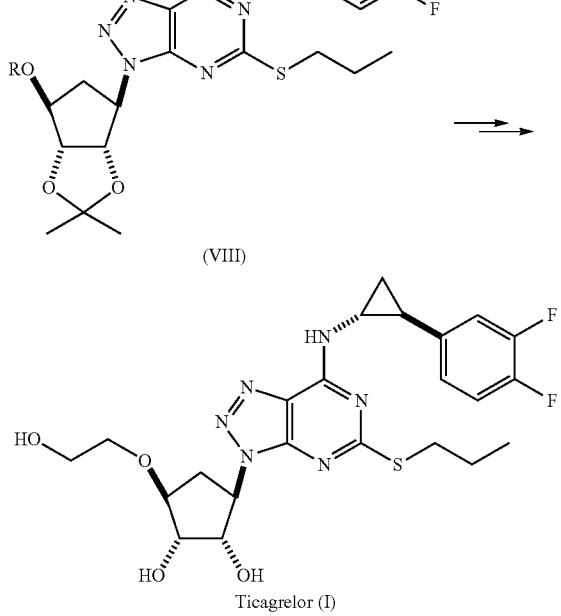

In addition, the invention also provides the following technical solution:

The chemical formula of 5-amino-1,4-disubstituted-1,2,3-triazole is shown as below (II):

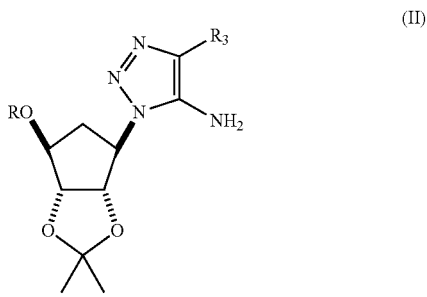

Of which, R is hydrogen (H), alkyl acetate (—$CH_2COOR_1$) or 2-alkoxy ethyl(—$CH_2CH_2OR_2$);

Of which, $R_3$ is formamido(—$CONH_2$), formyl(—COOH), cyano(—CN) or alkyl carbamate group (—$COOR_4$).

The substituent groups R1 and R4 in 5-amino-1,4-di-substituted-1,2,3-triazole (II) are independently selected from methyl, ethyl, propyl, butyl, allyl, phenyl, substituted phenyl, benzyl or substituted benzyl; a substituted alkyl group R2 is hydrogen (H), alkyl containing 1-6 carbon atoms, alkenyl containing 2-6 carbon atoms and alkynyl containing 2-6 carbon atoms, benzyl or substituted benzyl, trimethylsilyl, triphenylmethyl or substituted triphenylmethyl, tetrahydropyranyl or substituted tetrahydropyranyl or alkoxycarbonyl.

The chemical formula of dialkyl carbonate is as shown in the following formula (III),

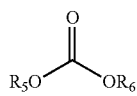

(III)

of which, R5 and R6 are independently selected from methyl, ethyl, n-propyl, isopropyl, allyl, t-butyl, n-butyl, phenyl, substituted phenyl, benzyl or substituted benzyl, preferably methyl or ethyl.

the alkali accelerators used in the cyclization reaction are sodium, sodium hydride, sodium methoxide, sodium ethoxide, sodium tert-butoxide, potassium tert-butoxide, potassium carbonate, potassium hydroxide or sodium hydroxide, preferably sodium ethoxide or potassium t-butoxide.

the chlorinating agent used in chlorination reaction is phosphorus oxychloride, phosphorus trichloride, phosphorus pentachloride, oxalyl chloride, thionyl chloride, benzoyl chloride, phthaloyl chloride, pivaloyl chloride or thionyl chloride, preferably phosphorus oxychloride or thionyl chloride.

the acid-binding agents used in chlorination reaction are triethylamine, pyridine, 2,6-lutidine, 4-dimethylaminopyridine, N-methylmorpholine, N-ethylmorpholine, diisopropylethylamine, 1,5-diazabicyclo[4.3.0]-non-5-ene, 1,8-diazabicyclo[5.4.0]-undec-7-ene or 1,4-diazabicyclo[2.2.2]octane. Preferably 2,6-lutidine or pyridine.

the solvents used in amination reaction are methanol, ethanol, isopropanol, n-butanol, isobutanol, t-butanol, tetrahydrofuran, 1,2-dioxane, dimethyl sulfoxide, acetonitrile or N, N-dimethylformamide, preferably acetonitrile or N, N-dimethylformamide.

This invention also provides the following subsidiary technical solution: the feeding molar ratio of intermediate (VI) to propanethiol (the two main raw materials for the propanethiolation reaction) is 1:1-2.0, preferably 1:1.2-1.5.

The alkali accelerators used in propanethiolation reaction are sodium hydride, sodium methoxide, sodium ethoxide, potassium t-butoxide, potassium carbonate, cesium carbonate, sodium hydroxide, potassium hydroxide, sodium amide, sodium bis(trimethylsilyl)amide, potassium bis(trimethylsily)amide, lithium bis(trimethylsily) amide or lithium diisopropylamide, preferably potassium hydroxide or sodium bis(trimethylsilyl)amide (NaHMDS).

In addition, the second objective of this invention is to provide a new Ticagrelor intermediate and preparation method thereof. The method for preparing the intermediate is simple, the reaction conditions are mild and easy to control, and raw materials of the preparation method are easily available, and the product yield and purity is high. It can simplify the whole process of synthesis, suitable for large-scale industrial production.

In order to achieve the second objective, the invention provides another technical solution: a method for preparing Ticagrelor, the intermediate is 5-amino-1,4-di-substituted-1,2,3-triazole as shown in the formula (II).

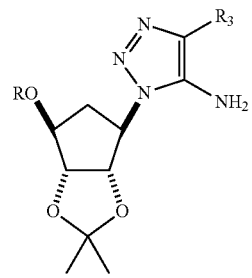

The preparation method comprise the following steps: a cyclization reaction between azide compound (IX) with cyano derivative (X) occurs, to obtain 5-amino-1,4-di-substituted-1,2,3-triazole (I).

$R_3$ = $CONH_2$, $COOH$, $CN$, $COOCH_3$ or $COOC_2H_5$, etc.

In addition, the preparation of above Ticagrelor intermediate (II) further comprises the subsidiary technical solution:

The starting material cyano derivative (X) is 2-cyanoacetamide (Xa), 2-cyanoacetic acid (Xb), malononitrile (Xc) or 2-cyano alkyl acetate (Xd).

The feeding ratio of azide compound (IX) to cyano derivative (X) (starting materials of the cyclization reaction) is 1:1-5, preferably 1:1.1-1.3.

the alkali accelerators used in cyclization reaction are sodium hydride, sodium methoxide, sodium ethoxide, sodium tert-butoxide, potassium tert-butoxide, potassium carbonate, triethylamine, pyridine, 2,6-lutidine, 4-dimethylaminopyridine, N-methylmorpholine, N-ethylmorpholine, diisopropylethylamine, 1,5-diazabicyclo[4.3.0]-non-5-ene, 1,8-diazabicyclo[5.4.0]-undec-7-ene or 1,4-diazabicyclo[2.2.2]octane; preferably sodium ethoxide or potassium t-butoxide.

the solvents used in the cyclization reaction are dichloromethane, chloroform, 1,2-dichloroethane, toluene, acetonitrile, tetrahydrofuran, methanol, ethanol, isopropanol, 1,2-dioxane, or tetrahydrofuran, preferably ethanol or tetrahydrofuran.

Furthermore, the third objective of the invention is to provide an azide compound and preparation method thereof that can be used for preparation of Ticagrelor intermediate.

The preparation method of azide compound is simple and the reaction conditions are mild and easy to control. Raw materials are easily available, and the product yield and chiral purity are high, which can simplify the whole synthesis process Ticagrelor, suitable for large-scale industrial production.

To achieve the third objective described above, the invention provides another technical solution: a method for preparing azide compound, the azide compound is 1-alkoxy substituted-2,3-acetone protected o-hydroxy-4-azido-cyclopentane as shown in the formula (IX):

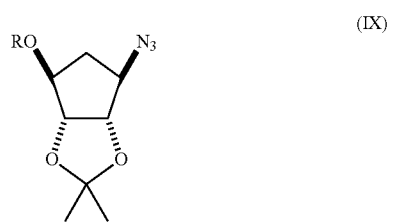

The preparation steps comprising: azido reaction of amino compound (XI) and azide reagent (XII), to obtain azide compound (IX).

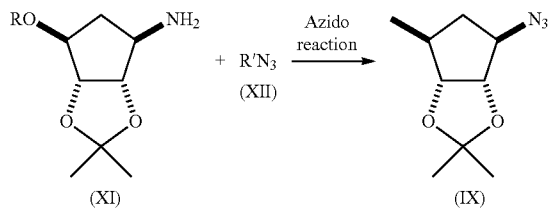

In addition, the preparation of azide compound (IX) also includes the following subsidiary technical solution:

four prochiral carbon atoms in azide compound (IX) can be single R configuration, single S configuration or its racemate respectively.

The feeding molar ratio of amino compound (XI) to azide reagent (XII) (starting materials of the azido reaction) is 1: 1-5, preferably 1:1.2-1.8.

The azide reagent (XII) is sodium azide, hydrazoic acid, imidazole azide sulfonyl(ImSO$_2$N3), trifluoromethanesulfonyl azide (TfN$_3$), p-toluenesulfonyl azide (TsN$_3$), methanesulfonyl azide (MsN$_3$) or trimethylsilyl azide (TMSN$_3$).

The alkali accelerators used in the azido reaction are sodium hydride, sodium methoxide, sodium ethoxide, sodium tert-butoxide, potassium tert-butoxide, potassium carbonate, triethylamine (TEA), pyridine, 2,6-lutidine, 4-dimethylaminopyridine (DMAP), N-methylmorpholine (NMM), N-ethylmorpholine (NEM), diisopropylethylamine (DIEA), 1,5-diaza-bicyclo[4.3.0]-non-5-ene (DBN), 1,8-diazabicyclo[5.4.0]-undec-7-ene (DBU) or 1,4-diazabicyclo [2.2.2]octane (DABCO).

the catalyst used in the azido reaction can be selected from copper chloride, nickel chloride, cobaltous chloride (II), zinc chloride, copper sulfate, nickel sulfate, cobaltous sulphate (II) or zinc sulfate.

The solvents used in the azido reaction are dichloromethane, chloroform, 1,2-dichloroethane, toluene, acetonitrile, tetrahydrofuran, methanol, ethanol, isopropanol, 1,2-dioxane or tetrahydrofuran.

For the preparation of Ticagrelor and intermediates thereof in the present invention, through the new intermediates and new synthetic routes, the preparation is fast and convenient, economical and environmentally friendly, with high product yield and purity, suitable for large-scale industrial production.

DETAILED DESCRIPTIONS OF THE PREFERRED EMBODIMENTS

The invention is described in details in combination with several preferred embodiments.

Embodiment I

Under the dry and nitrogen condition, 1-[3aR-(3aα,4α, 6α,6aα)-[[2,2-dimethyl-tetrahydro-4H-cyclopenta-1,3-dioxole-4-oxo-]ethanol]-6-yl]-5-amino-4-formamido-1,2,3-triazole (II) (3.27 g, 10 mmol), sodium ethoxide (2.72 g, 40 mmol) and 100 mL of absolute ethanol were added to a reaction flask, slowly heated to reflux, to react 3 hours. Within half an hour, dimethyl carbonate (III) (2.7 g, 30 mmol) was added to continue to reflux 6 hours. The ethanol was removed by distillation at atmospheric pressure, and repeated again with fresh ethanol, cooled down to room temperature; 50 mL of water was added, and adjusted to pH=6 with dilute acid while stirring, slowly crystallized 2 hours, filtered and the filter cake was recrystallized using 50% methanol, to get 2.55 g of off-white solid 9-[3aR-(3aα, 4α,6α,6aα)-[[2,2-dimethyl tetrahydro-4H-cyclopenta-1,3-dioxole-4-oxo-]ethanol]-6-yl]-2,6-dihydroxy-8-aza purine (IV), with a yield of 72.5%.

Embodiment II 1.77 g of 9-[3aR-(3aα,4α,6α, 6aα)-[[2,2-dimethyl tetrahydro-4H-cyclopenta-1,3-dioxole-4-oxo-]ethanol]-6-yl]-2, 6-dihydroxy-8-aza purine (IV) (5 mmol) and 15 mL of phosphorus oxychloride were added to a reaction flask, to start stirring, cooled down below 0° C., and then added dropwise 3.5 mL of 2,6-lutidine, and then slowly heated to 100° C. and maintained to react 9 hours while stirring. The phosphorus oxychloride was recovered under a reduced pressure, and after the residue was cooled down to room temperature, the reaction was quenched with ice water, extracted 3 times with methylene chloride, and the organic phases were combined, dried with anhydrous sodium sulfate. The solvent was recovered under reduced pressure to get 1.7 g of oily substance 9-[3aR-(3aα,4α,6α,6aα)-[[2,2-dimethyl tetrahydro-4H-cyclopenta-1,3-dioxole-4-oxo-] ethanol]-6-yl]-2,6-dichloro-8-aza-purine (V), with a yield of 87.5%.

Embodiment III 1.95 g of 9-[3aR-(3aα,4α,6α,6aα)-[[2,2-dimethyl tetrahydro-4H-cyclopenta-1,3-dioxole-4-oxo-]ethanol]-6-yl]-2, 6-dichloro-8-aza-purine (V) (5 mmol), 1.0 g of trans-(1R, 2S)-2-(3,4-difluorophenyl)cyclopropylamine (VI)(6 mmol) and 25 mL of acetonitrile were added to a reaction flask, to start stirring under room temperature and added with 1.5 mL of triethylamine, maintained at room temperature to react 12 hours while stirring, then the reaction ended with the TLC detection. The solution was concentrated under reduced pressure, and the residue was added ethyl acetate and water, and adjusted with dilute acid to pH=4. The organic phase was separated, and the aqueous phase was extracted 3 times with ethyl acetate. The organic phases were combined, washed with pure water and saline successively, dried and distilled under reduced pressure to recover the solvent, to get 2.25 g of oily substance 9-[3aR-(3aα,4α,6α,6aα)-[[2,2-dimethyl-tetrahydro-4H-cyclopenta-1,3-dioxole-4-oxo-]ethanol]-6-yl]-6-[[(1R,2S)-2-(3,4-difluorophenyl)cyclopropyl]amino]-2-chloro-8-aza purine (or named 2-{[(3aR,4S,6R,6aS)-6-{7-[[(1R,2S)-2-(3,4-difluorophenyl)cyclopropyl]amino]-5-chloro-3H-[1,2,3]triazolo[4,5-d]pyrimidin-3-yl}-2,2-dimethyl-tetrahydro-3aH-cyclopenta[d][1,3]-dioxol-4-yl]oxy}-1-ethanol) (VII), with a yield of 86.2%.

Embodiment IV 2.61 g of 9-[3aR-(3α,4α,6α,6aα)-[[2,2-dimethyl-tetrahydro-4H-cyclopenta-1,3-dioxole-4-oxo-]ethanol]-6-yl]-6-[[(1R,2S)-2-(3,4-difluorophenyl)cyclopropyl]amino]-2-chloro-8-aza purine (5 mmol), 0.46 g propanethiol (6 mmol) and 0.34 g potassium hydroxide (6 mmol) and 25 mL of ethanol were added to a reaction flask, to start reaction under room temperature while stirring, then the reaction ended with the TLC detection. The solution was concentrated under reduced pressure, and the residue was added dichloromethane and water, and adjusted with dilute acid to pH=6. The organic phase was separated, and the aqueous phase was extracted 3 times using dichloromethane. The organic phases were combined, dried and distilled under reduced pressure to recover the solvent, to get 2.54 g of oily substance 9-[3aR-(3aα,4α,6α,6aα)-[[2,2-dimethyl-tetrahydro-4H-cyclopenta-1,3-dioxole-4-oxo-]ethanol]-6-yl]-6-[[(1R,2S)-2-(3,4-difluorophenyl)cyclopropyl]amino]-2-mercapto-8-aza purine (or named: 2-{[(3aR,4S,6R,6aS)-6-{7-[[(1R,2S)-2 (3,4-difluorophenyl)cyclopropyl]amino]-5-propyl-mercapto-3H-[1,2,3]triazolo[4,5-d]pyrimidin-3-yl}-2,2-dimethyl-tetrahydro-3aH-cyclopenta[d][1,3]-dioxol-4-yl]oxy}-1-ethanol (VIII), with a yield of 90.4%.

Embodiment V 1.41 g of 9-[3aR-(3aα,4α,6α,6aα)-[[2,2-dimethyl-tetrahydro-4H-cyclopenta-1,3-dioxole-4-oxo-]ethanol]-6-yl]-6-[[(1R,2S)-2-(3,4-difluorophenyl)cyclopropyl]amino]-2-mercapto-8-aza purine (2.5 mmol) was added to a reaction flask at room temperature, and dissolved in 20 mL of methanol, added 10 mL of hydrochloric acid (3N) to react 24 hour while stirring at room temperature. The solution was adjusted to pH=7.0-7.5 with 30% sodium hydroxide solution, concentrated under reduced pressure to remove methanol, and extracted three times with ethyl acetate. The organic phases were combined and dried, and distilled under reduced pressure to recover the solvent, to obtain the crude product, which was recrystallized from ethyl acetate and n-hexane to get 0.85 g of white solid Ticagrelor (I) 0.85 g, with a yield of 65.4%.

Embodiment VI 1.0 g of 2-nitrile acetamide (Xa) (12 mmol), 1.0 g of sodium ethoxide (15 mmol) and 20 mL of absolute ethanol were added to a reaction flask at 0-5° C. and nitrogen atmosphere, after reacting 30 min, added dropwise 20 mL of solution of [3aR-(3α,4α,6α,6aα)]-6-azido-2,2-dimethyl-tetrahydro-4H-cyclopenta-1,3-dioxol-4-alcohol (IX) (2.0 g, 10 mmol) in ethanol; slowly warmed to reflux and maintained at reflux for 5 hours, then the reaction ended with the TLC detection. The solution was cooled down to room temperature, filtered to remove solids. The residue was precipitated after the addition of water, filtered and the solid was recrystallized from ethanol and ethyl acetate to get 2.4 g of 1-[3aR-(3aα,4α,6α,6aα)-[2,2-dimethyl-tetrahydro-4H-cyclopenta-1,3-dioxol-4-ol]-6-yl]-5-amino-4-formamido-1,2,3-triazole (II), with a yield of 84.8%.

Embodiment VII 1.0 g of 2-cyano-acetamide (Xa) (12 mmol), 0.8 g of sodium methoxide (15 mmol) and 20 mL of anhydrous methanol were added to a reaction flask at 0-5° C. and nitrogen atmosphere, after reacting 30 min, added dropwise 20 mL of solution of [3aR-(3aα,4α,6α,6aα)]-6-azido-2,2-dimethyl-tetrahydro-4H-cyclopenta-1,3-dioxol-4-alcohol (IX) (2.0 g, 10 mmol) in methanol; slowly warmed to room temperature and maintained 24 hours, then the reaction ended with the TLC detection. The solution was filtered to remove solids. The residue was precipitated after the addition of water, filtered and the crude product was recrystallized from isopropanol and ethyl acetate, to get 2.6 g of 1-[3aR-(3aα,4α,6α,6aα)-[2,2-dimethyl-tetrahydro-4H-cyclopenta-1,3-dioxol-4-ol]-6-yl]-5-amino-4-formamido-1,2,3-triazole (II), with a yield of 79.5%.

Embodiment VIII 0.8 g of malononitrile (Xc) (12 mmol), 1.8 g of potassium tert-butoxide (15 mmol) and 25 mL of dried tetrahydrofuran solvent were added to a reaction flask at 0-5° C. and nitrogen atmosphere, after reacting 30 min, added dropwise 30 mL of solution of [3aR-(3α,4α,6α,6aα)]-[6-azido-2,2-dimethyl-tetrahydro-4H-cyclopenta-1,3-dioxole-4-oxy]methyl acetate (IX) (2.7 g, 10 mmol) in tetrahydrofuran, slowly warmed to reflux and maintained at reflux for 6 hours, then the reaction ended with the TLC detection. The solution was filtered to remove solids. The residue was precipitated after the addition of water, filtered and the solid was recrystallized from ethanol and ethyl acetate to get 2.9 g of 1-[3aR-(3aα,4α,6α,6aα)-[[2,2-dimethyl-tetrahydro-4H-cyclopenta-1,3-dioxole-4-oxo-]methyl acetate]-6-yl]-5-4-cyano-1,2,3-triazole (II), with a yield of 86.1%.

Embodiment IX 1.73 g of [3aR-(3aα,4α,6α,6aα)]-6-amino-2,2-dimethyl-1,3-tetrahydro-cyclopenta-4H-dioxa cyclopentyl-4-ol (XI) (10 mmol), 2.76 g of potassium carbonate (20 mmol), 32 mg of copper sulfate (2% eq) and 25 mL of anhydrous methanol were added to a reaction flask, and added the solution of imidazole azide sulfonyl(XII) (2.1 g, 12 mmol) in methanol under 0° C. and nitrogen atmosphere, stirred at room temperature to react 5 hours, and the reaction ended with the TLC detection. The solution was concentrated under reduced pressure and the residue was recrystallized from n-hexane and ethyl acetate to get 1.8 g of [3aR-(3aα,4α,6α,6aα)]-6-azido-2,2-dimethyl-tetrahydro-4H-cyclopenta-1,3-dioxol-4-ol (IX), with a yield of 90.4%.

Embodiment X 2.17 g of [3aR-(3aα,4α,6α,6aα)]-6-amino-2,2-dimethyl-1,3-tetrahydro-cyclopenta-4H-dioxa cyclopentyl-4-ol (XI) (10 mmol), 2.76 g of potassium carbonate (20 mmol), 32 mg of copper sulfate (2% eq) and 25 mL of acetonitrile were added to a reaction flask, and added the solution of trifluoromethanesulfonyl azide (XII) (2.1 g, 12 mmol) in acetonitrile under 0° C. and nitrogen atmosphere, stirred at room temperature to react 3 hours, and the reaction ended with the TLC detection. The solution was concentrated under reduced pressure and the residue was recrystallized from n-hexane and ethyl acetate to get 2.25 g of [3aR-(3aα, 4α,6α,6aα)]-[6-azido-2,2-dimethyl-tetrahydro-4H-cyclopenta-1,3-dioxane-4-oxy]ethanol (IX), with a yield of 92.6%.

Embodiment XI 2.45 g of [3aR-(3aα,4α,6α,6aα)]-[6-amino-2,2-dimethyl-tetrahydro-4H-cyclopenta-1,3-dioxa-4oxo]methyl acetate (10 mmol) and 30 mL of dried tetrahydrofuran were added to a reaction flask, cooled down to 0° C. and under the nitrogen atmosphere, added dropwise a solution of sodium hydride in tetrahydrofuran and a solution of p-toluenesulfonyl azide (XII) (3.0 g, 15 mmol) in tetrahydrofuran successively. After the addition was complete, warmed to room temperature to react 30 hours while stirring, and the reaction ended with the TLC detection. The reaction was quenched with methanol under ice bath, poured down to water, adjusted to weakly acidic with hydrochloric acid, and extracted 3 times with ethyl acetate, dried over anhydrous sodium sulfate. The solution was concentrated under reduced pressure until dry, and recrystallized from hexane/ethyl acetate, to get 2.3 g of off-white solid [3aR-(3aα,4α, 6α,6aα)]-[6-azido-2,2-tetrahydro-4H-cyclopenta-1,3-dioxole-4-oxy]methyl acetate (IX), with a yield of 85.2%.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed is:

1. A method for preparing Ticagrelor(I),

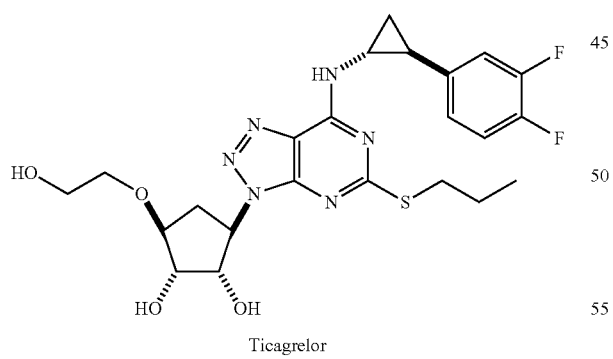

Ticagrelor wherein the preparation method comprises the following steps: a cyclization reaction of 5-amino-1,4-di-substituted-1,2,3-triazole (II) and dialkyl carbonate (III), to obtain 9-substituted-2,6-dihydroxy-8-azapurine (IV); chlorination of intermediate (IV), to obtain 9-substituted-2,6-dichloro-8-azapurine (V); an amination reaction of intermediate (V) and trans-(1R,2S)-2-(3,4-difluorophenyl)cyclopropanamine (VI) generates 9-substituted-6-amino-substituted-2-chloro-8-azapurine (VII); and a propanethiolation reaction of intermediate (VII) and propanethiol (VIII), to obtain Ticagrelor (I);

wherein the chemical formula of 5-amino-1, 4-disubstituted-1, 2,3-triazole is shown as below (II):

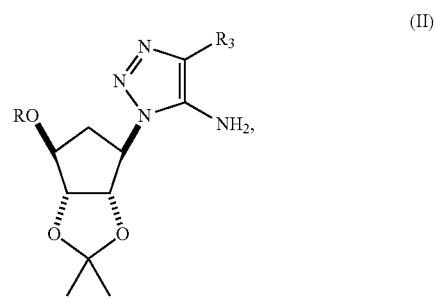

of which, R is hydrogen (H), alkyl acetate (—CH$_2$COOR$_1$) or 2-alkoxy ethyl(—CH$_2$CH$_2$OR$_2$);

of which, R$_3$ is formamido(—CONH$_2$), formyl(—COOH), cyano(—CN) or alkyl carbamate group (—COOR$_4$);

of which, each of R$_1$ and R$_4$ is independently selected from methyl, ethyl, propyl, butyl, allyl, phenyl, substituted phenyl, benzyl or substituted benzyl; R$_2$ is selected from hydrogen (H), alkyl containing 1-6 carbon atoms, alkenyl containing 2-6 carbon atoms and alkenyl containing 2-6 carbon atoms, benzyl or substituted benzyl, trimethylsilyl, triphenylmethyl or substituted triphenylmethyl, tetrahydropyranyl or substituted tetrahydropyranyl or alkoxycarbonyl;

wherein the chemical formula of dialkyl carbonate is as shown in the following formula (III),

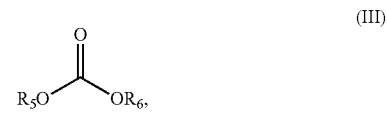

of which, R$_5$ and R$_6$ are independently selected from methyl, ethyl, n-propyl, isopropyl, allyl, t-butyl, n-butyl, phenyl, substituted phenyl, benzyl or substituted benzyl;

wherein the chemical formula of 9-substituted-2,6-dihydroxy-8-azapurine is shown in the following formula (IV):

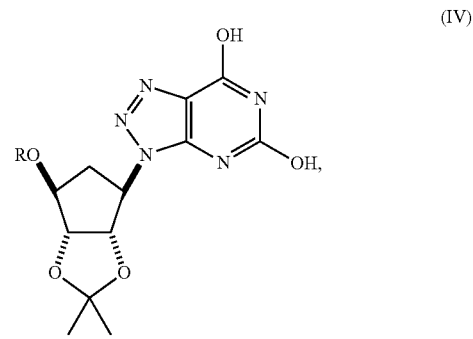

wherein the chemical formula of 9-substituted-2,6-dichloro-8-azapurine is shown in the following formula (V):

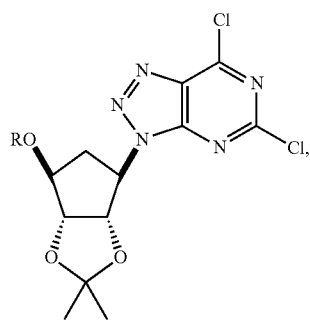

wherein the chemical formula of trans-(1R,2S)-2-(3,4-difluorophenyl)cyclopropanamine is shown in the following formula (VI):

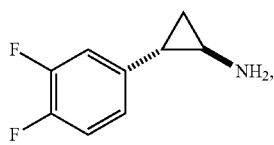

wherein the chemical formula of trans-(1R,2S)-2-(3,4-difluorophenyl)cyclopropanamine is shown in the following formula (VII):

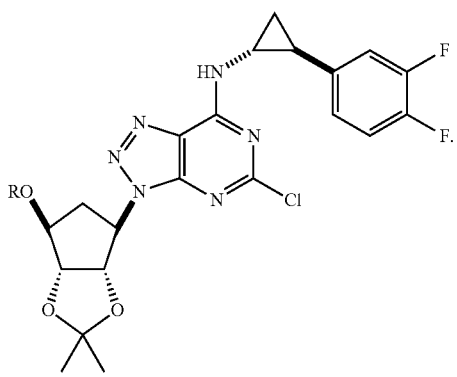

2. The method for preparing Ticagrelor according to claim 1, wherein the preparation of 5-amino-1, 4-disubstituted-1, the preparation of 2,3-triazole (II) comprises the following steps: cyclization reaction of azide compound (IX) and cyano derivative (X), to obtain 5-amino-1, 4-di-substituted-1, 2,3-triazole (II); Wherein the feeding ratio of azide compound (IX) to cyano derivative (X) is 1:1-5;
wherein cyano derivative (X) is 2-cyanoacetamide, 2-cyanoacetic acid, malononitrile or 2-cyano alkyl acetate.

3. The method for preparing Ticagrelor according to claim 2, wherein an alkali accelerator used in cyclization reaction is sodium hydride, sodium methoxide, sodium ethoxide, sodium tert-butoxide, potassium tert-butoxide, potassium carbonate, triethylamine, pyridine, 2,6-lutidine, 4-dimethylaminopyridine, N-methylmorpholine, N-ethylmorpholine, diisopropylethylamine, 1,5-diazabicyclo [4.3.0]-non-5-ene, 1,8-diazabicyclo[5.4.0]-undec-7-ene or 1,4-diazabicyclo [2.2.2]octane; and a solvent used in the cyclization reaction is dichloromethane, chloroform, 1,2-dichloroethane, toluene, acetonitrile, tetrahydrofuran, methanol, ethanol, isopropanol, 1,2-dioxane, or tetrahydrofuran.

4. The method for preparing Ticagrelor according to claim 2, wherein the chemical name of azide compound (IX) is 1-alkoxy-substituted-2,3-acetone protected o-hydroxy-4-azido-cyclopentane, and the chemical formula is shown as the formula (IX) below:

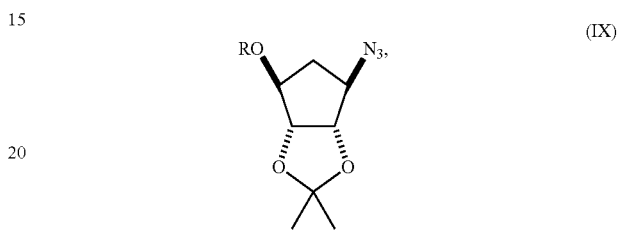

the preparation of the azide compound (IX) comprises the step: azido reaction of amino compound (XI) and azide reagent (XII), to obtain azide compound (IX).

5. The method for preparing Ticagrelor according to claim 2, wherein four prochiral carbon atoms in the azide compound (IX) can be single R configuration, single S configuration or its racemate.

6. The method for preparing Ticagrelor according to claim 2, wherein the azide reagent (XII) is sodium azide, hydrazoic acid, imidazole azide sulfonyl, trifluoromethanesulfonyl azide, p-toluenesulfonyl azide, methanesulfonyl azide or trimethylsilyl azide.

7. The method for preparing Ticagrelor according to claim 2, wherein a feeding molar ratio of amino compound (XI) to azide reagent (XII) is 1: 1-5 in the azido reaction; wherein an alkali accelerator used in the azido reaction is sodium hydride, sodium methoxide, sodium ethoxide, sodium tert-butoxide, potassium tert-butoxide, potassium carbonate, triethylamine, pyridine, 2,6-lutidine, 4-dimethylaminopyridine, N-methylmorpholine, N-ethylmorpholine, diisopropylethylamine, 1,5-diazabicyclo bicyclo [4.3.0]-non-5-ene, 1,8-diazabicyclo [5.4.0]-undec-7-ene or 1,4-diazabicyclo [2.2.2]octane; wherein the catalyst used for azido reaction can be selected from copper chloride, nickel chloride, cobaltous chloride(II), zinc chloride, copper sulfate, nickel sulfate, cobaltous sulphate(II) or zinc sulfate; wherein a solvent used in azido reaction can be dichloromethane, chloroform, 1,2-dichloroethane, toluene, acetonitrile, tetrahydrofuran, methanol, ethanol, isopropanol, 1,2-dioxane or tetrahydrofuran.

8. The method for preparing Ticagrelor according to claim 1, wherein: an alkali accelerator used in the cyclization reaction is sodium, sodium hydride, sodium methoxide, sodium ethoxide, sodium tert-butoxide, potassium tert-butoxide, potassium carbonate, potassium hydroxide or sodium hydroxide.

9. The method for preparing Ticagrelor according to claim 1, wherein a chlorinating agent used in chlorination reaction is phosphorus oxychloride, phosphorus trichloride, phosphorus pentachloride, oxalyl chloride, thionyl chloride, benzoyl chloride, phthaloyl chloride, pivaloyl chloride or thionyl chloride.

10. The method for preparing Ticagrelor according to claim 1, wherein an acid-binding agents used in chlorination reaction is triethylamine, pyridine, 2,6-lutidine, 4-dimethylaminopyridine, N-methylmorpholine, N-ethylmorpholine, diisopropylethylamine, 1,5-diazabicyclo [4.3.0]-non-5-ene, 1,8-diazabicyclo [5.4.0]-undec-7-ene or 1,4-diazabicyclo [2.2.2]octane.

11. The method for preparing Ticagrelor according to claim 1, wherein a feeding molar ratio of 9-substituted-6-amino-substituted-2-chloro-8-azapurine (VII) to propanethiol (VIII) is 1:1-2.0; wherein an alkali accelerator used in propanethiolation reaction is sodium hydride, sodium methoxide, sodium ethoxide, potassium t-butoxide, potassium carbonate, cesium carbonate, sodium hydroxide, potassium hydroxide, sodium amide, sodium bis(trimethylsilyl) amide, potassium bis(trimethylsily)amide, lithium bis(trimethylsily)amide or lithium diisopropylamide.

\* \* \* \* \*